US009554780B2

(12) United States Patent
Gonçalves Pereira Nobre et al.

(10) Patent No.: US 9,554,780 B2
(45) Date of Patent: Jan. 31, 2017

(54) PORTABLE DEVICE FOR THE STORAGE, TRANSPORT AND RECUPERATION OF BIOLOGICAL MATERIAL

(75) Inventors: Rui Jorge Gonçalves Pereira Nobre, Outil (PT); Hugo João Marques Prazeres, Serpins (PT); Rui Pedro Marques Da Costa, Magualde (PT); Luís Carlos Gonçalves Pereira Nobre, Outil (PT)

(73) Assignee: INFOGENE LDA., Coimbra (PT)

( * ) Notice: Subject to any disclaimer, the term of this patent is extended or adjusted under 35 U.S.C. 154(b) by 510 days.

(21) Appl. No.: 14/002,617

(22) PCT Filed: Mar. 1, 2012

(86) PCT No.: PCT/PT2012/000006
§ 371 (c)(1),
(2), (4) Date: Aug. 30, 2013

(87) PCT Pub. No.: WO2012/118392
PCT Pub. Date: Sep. 7, 2012

(65) Prior Publication Data
US 2013/0337439 A1 Dec. 19, 2013

(30) Foreign Application Priority Data
Mar. 1, 2011 (PT) .......................... 105553

(51) Int. Cl.
*B01L 3/00* (2006.01)
*A61B 10/02* (2006.01)
(Continued)

(52) U.S. Cl.
CPC ........... *A61B 10/02* (2013.01); *A61B 10/0045* (2013.01); *B01L 3/5021* (2013.01); *B01L 3/5029* (2013.01);
(Continued)

(58) Field of Classification Search
CPC ............... A61B 10/0051; A61B 10/02; A61B 2010/0003; A61B 10/0096; A61B 10/0045; A61B 2010/0216; A61B 10/00; A61B 2010/0074; A61B 10/0038; B01L 2300/027; B01L 2300/044; B01L 2300/0672; B01L 2400/0683; B01L 3/5029; B01L 3/50825; B65D 51/224; C04B 2235/6565; C04B 2237/345; C04B 2237/408; A61J 1/201; A61J 1/2013; A61J 1/2089; A61J 1/1418; A61J 1/2086; A61J 1/2093; G01N 2001/028; C12M 33/02; A61F 13/38
See application file for complete search history.

(56) References Cited

U.S. PATENT DOCUMENTS 3,586,064 A 6/1971 Brown et al.
7,618,591 B2 * 11/2009 Slowey et al. ................ 422/412
(Continued)

FOREIGN PATENT DOCUMENTS

JP 2007-170979 A 7/2007
WO 00/65022 A1 11/2000
(Continued)

OTHER PUBLICATIONS

International Search Report for PCT/PT2012/000006 dated Jun. 19, 2012.

*Primary Examiner* — Erik B Crawford
(74) *Attorney, Agent, or Firm* — Sughrue Mion, PLLC (57) ABSTRACT

The present invention refers to a portable device for the collection of biological samples. The device comprises a receptacle (8) with a cover (2), which comprises a pierceable area (3) and may include a collection instrument (1), comprising a rod (4), and a collection arrangement at the end, which may include a solid matrix, for instance a sponge or a tampon (5). The receptacle (8) has a rounded or conical (Continued)

shaped bottom (10), at the center of which there is a conical or rounded-shaped projection (11), with one or more holes (12). The bottom of the receptacle (8) is in contact with a collector recipient through a system of close-aperture, which may comprise screw or a fitting system with protrusions (13). In this way, the device referred in the present invention allows for the collection, storage, transportation and separation of biological material without significant manipulation and without risk of cross-contamination.

7 Claims, 5 Drawing Sheets

(51) Int. Cl.
*A61B 10/00* (2006.01)
*G01N 1/02* (2006.01)
*G01N 1/40* (2006.01)
*G01N 15/06* (2006.01)

(52) U.S. Cl.
CPC ........ *G01N 1/02* (2013.01); *G01N 1/40* (2013.01); *G01N 15/0656* (2013.01); *A61B 10/0096* (2013.01); *A61B 2010/0087* (2013.01); *B01L 2200/025* (2013.01); *B01L 2200/026* (2013.01); *B01L 2200/0689* (2013.01); *B01L 2300/044* (2013.01); *B01L 2300/046* (2013.01); *B01L 2300/0609* (2013.01); *B01L 2300/087* (2013.01); *B01L 2300/0832* (2013.01); *B01L 2400/0409* (2013.01); *G01N 2001/028* (2013.01)

(56) References Cited

U.S. PATENT DOCUMENTS

| 8,387,810 B2* | 3/2013 | Livingston et al. | .......... 215/250 |
| 8,722,330 B2* | 5/2014 | Ahlquist | ............ A61B 10/0038 435/325 |

FOREIGN PATENT DOCUMENTS

| WO | 2008/143570 A1 | 11/2008 |
| WO | 2010/027283 A1 | 3/2010 |
| WO | 2011/018658 A1 | 2/2011 |

* cited by examiner

PORTABLE DEVICE FOR THE STORAGE, TRANSPORT AND RECUPERATION OF BIOLOGICAL MATERIAL

CROSS REFERENCE TO RELATED APPLICATIONS

This application is a National Stage of International Application No. PCT/PT2012/000006 filed Mar. 1, 2012, claiming priority based on Portuguese Patent Application No. 105553 filed Mar. 1, 2011, the contents of all of which are incorporated herein by reference in their entirety.

TECHNICAL FIELD OF THE INVENTION

The present invention refers to a portable device for the collection, storage, transport and separation of biological samples.

STATE OF THE ART

In 1990's, epidemiologic and molecular biology studies have established a causal relation between the persistent infection by high risk types of the Human Papillomavirus (HPV) and the development of several types of cancer in the anogenital and oropharyngeal regions, among which are cancer of the cervix, vulva, vagina and anus, as well as cancers in the oral cavity. Today it is known that HPV is present in virtually all cases of cervical cancer and in about 40% of carcinomas of the vulva. There is also a direct association between HPV infection and cancer of the anus, vagina, penis, as well as cancers of the oropharynx.

Overall, HPV is the etiological agent underlying a broad spectrum of human carcinomas. For this reason, the detection of HPV plays a crucial role in routine clinical practice. Aside from the sensitivity and specificity of the detection assays, other factors are extremely important when considering detection of HPV and/or analysis of other infectious pathogenic agents and/or other cancer biomarkers.

In particular, the steps of collecting and storing the biological samples are critical since them are the first to be performed and thus influence all the subsequent analytical steps. Therefore, it is essential for patient compliance that a non-invasive or a minimally invasive procedure is employed for the collection of samples. On the other side, a minimal required quality and quantity of the biological sample needs to be ensured for the analysis to be performed.

A variety of methods has been developed for the collection of biological samples intended for subsequent detection of HPV, of other infectious agents and/or of cancer biomarkers. For example, in the cervical cancer screening programs the cervicovaginal samples are usually obtained through the use of collection devices, such as: brushes, swabs, sponges or vaginal tampons. As comfortable as possible, these devices are inserted into the vaginal tract where they are turned or left for a given period of time. Afterwards, they are removed and placed on a tube until processing.

In the case of the oral tract, a given user can also collect biological samples consisting of shed cells from the mouth or tongue epithelia as well as from saliva, all of which having the purpose of detecting HPV and/or other infectious agents and/or cancer biomarkers.

The current methodologies used to separate the cells from the collection devices, for example, from a tampon, have been proven problematic, very inefficient, time-consuming and highly susceptible to cross-contamination. These drawbacks come from the fact that the collection device is placed inside a transport tube, which is sent to the laboratory where the analytical determination is made. At the laboratory the transport tube is opened by the lab technician, who further manipulates the collection device so as to place it in a new tube (recovery tube), intended for the recovery of the biological sample. Aside from the fact that this manipulation is time-consuming, when performed simultaneously on several samples it introduces a high risk of cross-contamination.

The recovery of the biological material is performed by washing the collection device using a liquid solution that is pipetted into the recovery tube. This step comprises a further step of manipulation and another likely source of contamination.

Afterwards, the biological material that is inside the recovery tube, together with the collection device, is recovered by centrifugation. This procedure is less efficient, since the collection device (being a tampon or swab) always absorbs some part of the biological sample.

Next, in the process of recovering the biological sample, it is necessary to open the recovery tube once again in order to remove the supernatant. In this step it is frequent that the presence of the collection device inside the recovery tube hampers the correct pipetting.

Finally, it is necessary to dissolve the biological material and to place it in a new tube, where it is processed for analysis.

Overall, all the former procedures represent excessive manipulation and comprise high risk of cross-contamination.

A few ways to solve some of the problems raised by the above-mentioned drawbacks have been proposed. Examples of such proposals are found in documents EP1939604A1 and US2010113974A1.

Document EP1939604A1 presents a device for collection of biological samples comprising a recovery tube with an open end and a means to close that end and an element connecting the other end to a solid matrix over which the biological sample can be deposited. The matrix-deposited sample is transferable, at least in part, to a liquid or a liquid-solving state, through changing a physicochemical property of the matrix environment, but without disintegration of the matrix. However, in this device, since the collected biological material is in direct contact with the matrix, it is difficult to separate them both. Besides, the collection device is not properly attached to the recovery tube, considerably reducing the efficiency of the collection step.

Document US2010113974 A1 discloses a device for collecting biological samples from a bull's penis and foreskin comprising: a) a tip, shaped to scratch the surface of the mucosa, collecting biological material by pulling the tip in the collection region; and b) an applicator, that is connected to the collection tip by means of a rod. This device comprises the disadvantage that it is not conceived in such a way so that the biological sample is easily separated from the collection tip.

SUMMARY OF THE INVENTION

So, in order to solve the disadvantages of the above-mentioned devices, the present invention proposes a device according to claim 1.

The device referred in the present invention solves the problem of excessive manipulation and risk of contamination through the combination, in a single portable and assembled device, of all the characteristics necessary for collection, storage, transport and separation of biological materials, which can be used to perform a number of analytic determinations, for example the detection of the human papillomavirus.

DESCRIPTION OF THE INVENTION

The present invention concerns a device for the collection of biological samples.

Figure 1:
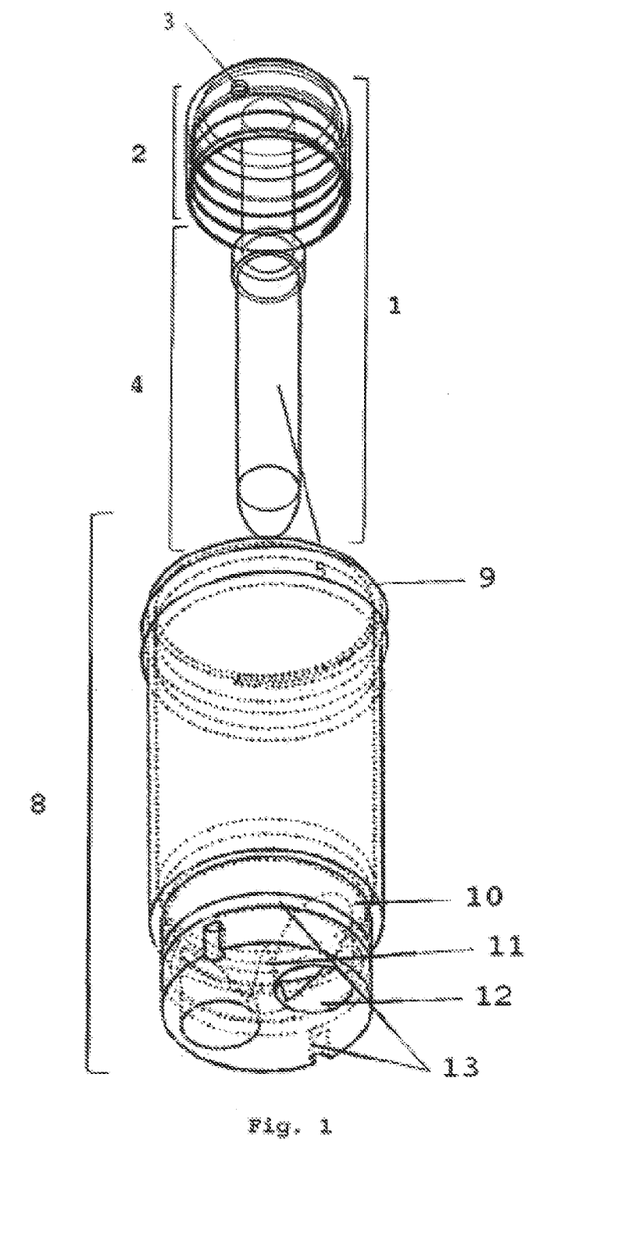
FIG. 1—represents a device in accordance with the present invention, comprising a receptacle (8) with a cover (2). This said cover comprises a pierceable area (3). The said receptacle (8) presents a conical or round-shaped end (10), at the center of which there is a conical or rounded-shape protuberance (11), and one or more holes (12). One end of the receptacle (8) is connected with a collector recipient through a close-aperture system, which comprises a screw or a fitting system with protrusions (13).

The device in the present invention comprises a receptacle (8) with a cover (2). This cover comprises a pierceable area (3). The receptacle (8) presents a conic or rounded-shape bottom (10), at the centre of which there is a conical or rounded-shaped protuberance (11), and one or more holes (12). The end of the receptacle (8) interacts with a collector recipient through a close-aperture system, which comprises a screw or a fitting system with protrusions (13).

Figure 2:
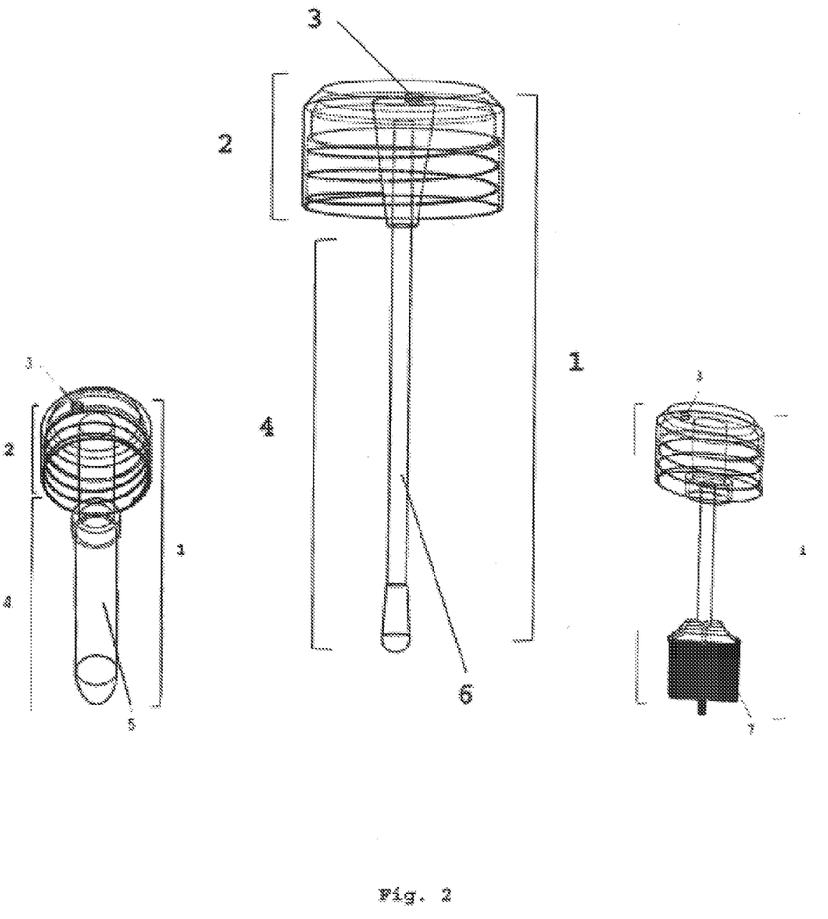
FIG. 2—represents a device, in accordance with the present invention, in which the said cover (2) of the said device comprises a system for functional connection to the said receptacle (8), comprising a screw, and includes a pierceable area (3). The said cover (2) comprises a collection instrument (1), with a rod (4) that, at one end, presents a collection arrangement, which comprises, a sponge or a tampon (5), a swab (6) or a brush (7).
Figure 4:
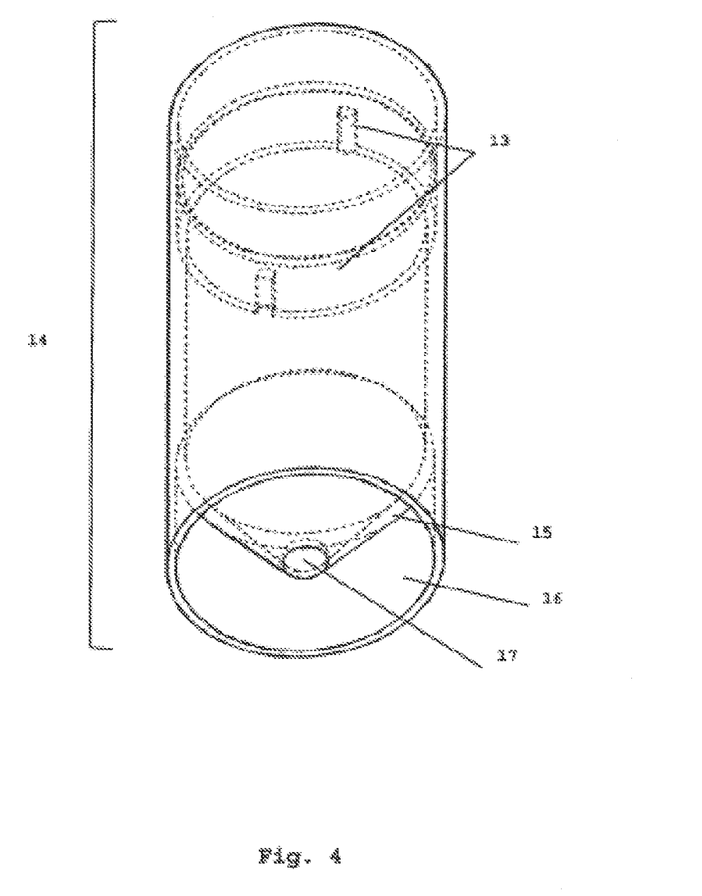
FIG. 4—represents a device, in accordance with the present invention, in which the said collector recipient (14) is functionally assembled to the receptacle (8) through a fitting system with protrusions (13), and presents a conical end (15), with the possibility of including a pierceable area at the bottom (17), with an edge that creates a flat contact surface (16).

The collector recipient (14), which receives the transferred biological sample, comprises a conical or rounded-shape bottom (15), with an edge that creates a flat contact surface (16), being removable, but functionally connected to the receptacle (8), through a close-aperture system that may comprise a screw or a fitting systems with protrusions (13). In one specific embodiment of the present invention, the said cover (2) comprises a collection instrument (1), with a rod (4), that presents a collection arrangement at the end, which may comprise a solid matrix, for example a sponge or a vaginal tampon (5), a swab (6) or a brush (7).

In the present invention, a "tampon" consists of an object with an absorption function, which can be inserted and removed into and out-off body orifices, and allows for the collection of cells and/or liquids. Essentially the tampon is composed of an hydrophilic material destined for absorption, for example rayon, cotton, wool, silk, cellulose fiber, paper or a mixture of hydrophilic materials, such as the ones mentioned above, along with hydrophobic materials, for example polyester, polyamide, acrylic or polyolefin.

In the present invention, a "sponge" consists of an object with an absorption function, which can be inserted and removed into and out-off body orifices, and allows for the collection of cells and/or body liquids, composed of a material with pores of regular or irregular size, randomly distributed in a flexible or solid hydrophilic matrix, destined to absorption, such as polyvinyl alcohol (PVA), cellulose fiber or expanded polyester.

In the present invention, a "swab" consists of an object composed of a rod, with, for example a cylindrical shape or one with a variable number of angles, with one or both ends covered in a absorbing solid matrix, which allows the absorption of cells and/or body liquids. These ends are essentially composed of a hydrophilic material destined for absorption, for example rayon, cotton, wool, silk, cellulose fiber, paper or it can comprise a mixture of the above-mentioned hydrophilic materials along with hydrophobic materials, such as polyester, polyamide, acrylic or polyolefin.

In the present invention, a "brush" consists of an object composed of a rod, with for example a cylindrical shape or one with a variable number of angles, composed of polypropylene or other polymer, with an end filled with a pattern of short or long, thick or thin, protrusions, made of a material compatible with the function of collecting cellular samples, for example urethane or any other polymer that is adequate for this function.

In one of the preferred forms of the present invention the collector recipient (18) comprises a pierceable area at its bottom (17). In this specific case, it is possible to directly recover the biological sample through the perforation of this area, without disassembling the device, conferring features that make the separation process amenable for automation and favoring speed in the overall process.

Figure 5:
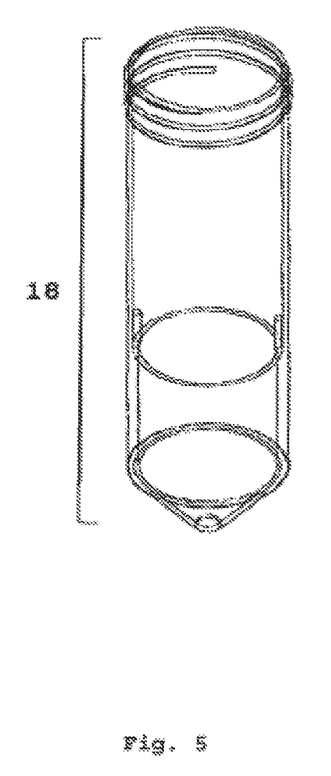
FIG. 5—represents a device, in accordance with the present invention, in which the said collector recipient (18) is dimensioned in height and diameter so that the said receptacle (8) can be placed inside it.

In another embodiment of this invention, the collector recipient (18) has height and diameter large enough so that the receptacle (8) can be placed inside the said collector recipient. In this specific case, an extra layer of protection is conferred by the collector recipient, which protects the receptacle and the biological sample from physical and chemical changes. For example, upon centrifugation, the potential for deformation is mainly concentrated in the collector recipient and not in the receptacle.

Figure 3:
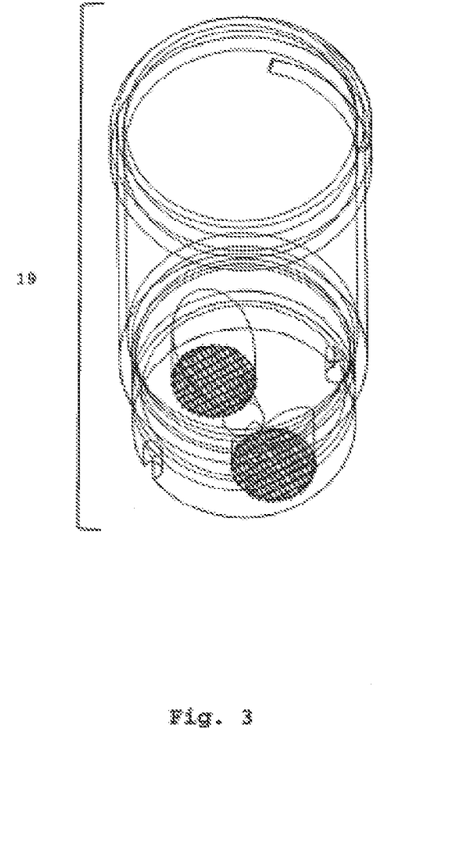
FIG. 3—represents a device, in accordance with the present invention, in which the said holes in the said receptacle (6) present a net configuration (19).

In another form of the present invention, the holes (12) in the receptacle (8) are filled with matrix comprising a net or a filter (19), of variable caliber, allowing for a selective separation of the biological sample. In this specific case, the said filter or net is dimensioned in such a way that certain components of the biological sample are selectively retained. For example cells can be retained, while the said net or filter is permeable to the extracellular medium or fluids. The selectivity can be modulated by the caliber of the matrix filling the holes in the receptacle.

In another form of the present invention the holes (12) in the receptacle (8) are filled with a chemically treated solid matrix that allows for the inactivation of pathogens, cell lysis, protein denaturation and capture of nucleic acids at room temperature. In this case the solid matrix may comprise, for example an "FTA paper", according to document U.S. Pat. No. 5,496,562.

In the present invention, "FTA paper" refers to a solid matrix, for example a cellulose absorbing paper (filter paper) or a mixture of synthetic plastic, over which a chemical composition is deposited in order to protect nucleic acids against degradation.

In another form of this invention, the receptacle (8) is produced of materials with distinct degree of opacity, which allows for protection of the enclosed sample from visible and ultraviolet light.

The addition of materials such as for example as zinc oxide or pigments or others that prevent the passage of light (visible or ultraviolet) reduces the amount of radiation that reaches the sample, increasing its preservation time.

Biological samples, such as cells, blood, cervicovaginal mucus, saliva or biological materials transported in exhaled breath, which are contained in a matrix made of cellulose, cotton, polymers, synthetic or natural fiber under the form or shape of a tampon, swab, sponge, paper, or brush, can be processed employing the device of the present invention, so as to perform any of several analytic determinations, through the collection, storage, transport and separation of biological samples.

In one of the forms of the present invention, the device is used with the purpose of collecting a biological sample for the detection of Human Papillomavirus in the setting of cervical cancer screening.

In the present invention, when a solid matrix, for example a tampon, is used for sample collection, both the said collection instrument, the receptacle and the collector recipient are initially assembled and functionally connected, nonetheless they remain removable from each other so that, at the end of the separation the biological sample is recovered at the bottom of the collector recipient separately of the collection instrument.

Additionally, in the present invention, the said receptacle presents one or more conical or rounded-shape protuberances that confer the advantage that the said collection instrument is stabilized inside the receptacle. Furthermore, these said conical or rounded-shape protuberances can guide the biological material contained in the said collection instrument towards the said holes in the end of the said receptacle, allowing for the transference of the biological material into the said collector recipient, resulting in an overall efficient recovery of the biological sample through a procedure that eliminates the chances of cross-contamination. Summing up, the device of the present invention allows for the collection of biological materials, along with its simultaneous storage, transport and separation from the collection instrument, all taking part within the same device.

The biological samples are initially collected through establishing contact of the said collection arrangement with the area of origin of the sample to be taken, for example from the cervicovaginal or oropharyngeal mucosa.

The biological sample can also be directly deposited within the said receptacle (8), for example, in the case of exhaled breath, saliva, urine or stool samples.

The said collection instrument is manually inserted, for example, in the vagina, where it can be left to absorb a biological sample for a given period of time, for example for 5 minutes. The said collection instrument can also be rotated, for example to at least for 180 degrees. After absorption and/or rotation the said collection instrument is removed.

After collection of the respective biological, the said collection instrument (1) is inserted within the said receptacle (8), which is assembled onto the said collector recipient (14), and the said cover (2) is screwed.

This portable assembly, in which the biological sample and the said collection instrument are stored, can be easily transported. Upon arrival at the laboratory or any other site of destiny for treatment, and without any other sort of manipulation, the said cover (2) is directly pierced with a pipette tip at the said pierceable area (3) allowing for the introduction of a given volume of a specific solution or reagent designed to wash the said collection instrument (4) while inside the said receptacle (8).

Next, a centrifugation is performed, for example at 10,000 rotations per minute for a short period of time, for example 5 minutes. Through centrifugation, the biological sample is directed by the said conical protuberance (11) into the said holes (12) in the end of the receptacle and recovered at the bottom of the collector recipient (14).

Afterwards, the receptacle (8) is disassembled from the collector recipient (14) and the excess washing reagent is removed, for example with the aid of a micropipette, and the recovered biological sample is then ready to be processed for any analytical determination, including the extraction and detection of nucleic acids derived from infectious agents, for example deoxyribonucleic acid (DNA) derived from Human Papillomavirus (HPV).

EXAMPLES

Example 1

Device in which the Said Collection Arrangement for Collecting the Biological Sample Comprises a Said Tampon In one specific embodiment of the present invention, the device is used for collection of genital samples. In this form of the invention, the collection arrangement, at the end of the said collection instrument, comprises a said tampon. The sample is collected by absorption into the tampon matrix of shed cells and cervicovaginal mucus. The tampon is inserted through the vagina into the genital tract. It is kept in the cervicovaginal milieu for a given period of time, for example 15 minutes, after which it is removed. The use of the said tampon has the advantage of conferring a high capacity for absorption, which results in the collection of significant amounts of biological material. Furthermore the use of the said tampon causes no pain or discomfort, since collection is not made by any sort of friction. After collection of the biological sample, the said tampon (1) is inserted within the said receptacle (8) of the device, which has been previously assembled onto the collector recipient (14), and the said cover (2) is screwed.

Example 2

Device in which the Said Collection Arrangement for Collecting the Biological Sample Comprises a Said Brush In one specific embodiment of the present invention, the device is used for collection of genital samples. In this form of the invention, the collection arrangement, at the end of the said collection instrument, comprises a said brush. The biological sample is collected through contact and/or friction of the said brush with the intended point of origin of the sample, for example the cervical mucosa. The said collection instrument, comprising a said brush at the end is inserted through the vagina. While the said collection instrument is inserted into the genital tract, it is rotated so as to collect cells and mucus by scrapping the genital mucosa at an intended area of origin of the sample, for example the cervix. The use of the said brush enables the advantage that the large number of protrusions that compose the said brush collection arrangement largely increases the area of the surface of contact with the mucosa, with each of the said protrusions being able to shed cells from the mucosa, thus significantly increasing the quantity of collected material. After collection of the biological sample, the said brush (1) is inserted within the said receptacle (8) of the device, which has been previously assembled onto the collector recipient (14), and the said cover (2) is screwed.

Example 3

Device in which the Said Collection Arrangement for Collecting the Biological Sample Comprises a Said Sponge In one specific embodiment of the present invention, the device is used for collection of genital samples. In this form of the invention, the collection arrangement, at the end of the said collection instrument, comprises a said sponge.

In this form of the invention, a sample of cells and/or mucus is collected through absorption upon physical contact of the said sponge with the mucosa of the cervix and/or vagina. In practical terms, the said sponge is inserted in the genital tract, through the vagina and it is then compressed and subsequently expanded in a way that, during expansion the said sponge absorbs biological material into its composing pores. The use of a said collection arrangement comprising a said sponge has the advantage that, because of the large number of pores composing the said sponge, the volume to store collected material is very high and the amount of collected material is highly significant. Moreover, the use of a said collection arrangement comprising a said sponge has the advantage of causing little or no pain, since collection is not made by friction against the mucosa. After collection of the biological sample, the said sponge (1) is inserted within the said receptacle (8) of the device, which has been previously assembled onto the collector recipient (14), and the said cover (2) is screwed.

Example 4

Device in which the Said Collection Arrangement for Collecting the Biological Sample Comprises a Said Swab In one specific embodiment of the present invention, the device is used for collection of genital samples. In this form of the invention, the collection arrangement, at the end of the said collection instrument, comprises a said swab.

In this form of the invention the sample is collected through contact, friction and absorption into the matrix of the said swab of cells and mucus. The swab is inserted into the vagina through the said rod. With the swab inserted inside the genital tract, the said swab is frictioned and rotated against the genital mucosa, for example the cervix, so that it captures and absorbs biological materials. The use of a said collection arrangement comprising a said swab has the advantage of generating a very narrow collection instrument, which is easily inserted into the genital tract. After collection of the biological sample, the said swab (1) is inserted within the said receptacle (8) of the device, which has been previously assembled onto the collector recipient (14), and the said cover (2) is screwed.

Example 5

Device for Collection of Biological Materials in the Oropharynx

In one of the forms of the present invention, the device is used for collection of samples from the oral cavity and/or the pharynx. In this form of the invention, saliva, shed cells or mucus in the oral cavity are collected through contact and/or friction and/or absorption by the said collection instrument (1) when inserted into, and subsequently removed out of the oral cavity. After collection of the oropharyngeal biological samples, the said collection instrument (1) is inserted within the said receptacle (8) of the device, which has been previously assembled onto the collector recipient (14), and the said cover (2) is screwed. This form of the invention has the advantage of putting together, in the same device, the steps for collection, storage and separation of materials derived from the oropharynx.

Example 6

Device for Collecting Saliva Samples

In one of the forms of the present invention, the said device is used to collect saliva samples.

In this form of the present invention, saliva spitted by the user of the device is deposited directly into the said receptacle. The saliva and biological materials contained therein are directed by the said conical or rounded-shape protuberance (11) towards the said holes (12) in the said receptacle. The said holes can be filled with a chemically treated, solid matrix, for example "FTA paper", which captures and stores the biological materials contained in the saliva.

While not in use, the receptacle is enclosed with a cover (2) that does not necessarily need to have a collection instrument attached to it. This form of the invention has the advantage of allowing analytical determinations on biological materials transported in saliva. Furthermore this form of the invention has the advantage of allowing collection and storage of a saliva sample in the same device.

Example 7

Device for Collection of Biological Material Carried in the Exhaled Breath

In one of the forms of this invention, the said device is used to collect biological materials transported in the exhaled breath. In this form of the invention, the user of the device exhales directly into the said receptacle for a given period of time, for example 10 minutes. The biological materials carried in the exhaled breath are directed into the said holes in the receptacle (12), which are filled with a chemically treated solid matrix, for example "PTA paper", that captures and stores the biological materials carried in the exhaled breath. The exhaled air leaves the device through the said perforated bottom (17) of the said collector recipient. While not in use, the receptacle is enclosed with a cover (2) that does not necessarily need to have a collection instrument attached to it. This form of the invention has the advantage of allowing analytical determinations on biological materials originated in tissues of the respiratory tract, for example, lung, trachea or larynx. Furthermore this form of the invention has the advantage of allowing collection and storage of this sort of sample in the same device.

The invention claimed is:

1. A process for recovering a treated biological sample, comprising the following steps:
   a) providing a device for collection and treatment of biological samples comprising:
      a receptacle with a conical or round-shaped end, at the center of which there is a conical or rounded shape protuberance and one or more holes;
      a cover to be operably connected with the receptacle, which comprises a pierceable area, the cover being connected to a rod and a collection arrangement disposed at a distal end of the rod; and
      a tube that mates with the conical or round-shaped end of the receptacle;
   b) contacting the collection arrangement with anogenital, oropharyngeal or respiratory areas of origin of a biological sample to be treated;
   c) inserting the collection arrangement comprising the biological sample to be treated into the receptacle;
   d) assembling the receptacle comprising the collection arrangement onto the tube and connecting the cover;
   e) piercing the pierceable area of the cover and introducing a treatment solution into the receptacle to treat the biological sample;
   f) centrifuging the device;
   g) recovering the treated biological sample at a bottom of the tube.

2. The process according to claim 1, further comprising removing the treatment solution through pipetting.

3. The process according to claim 1, further comprising detecting at least one of nucleic acids or proteins in the treated biological sample.

4. The process according to claim 1, wherein the one or more holes of the receptacle are filled with at least one of a solid, fiber or gel matrix for at least one of storage, treatment or selective separation of the biological sample.

5. The process according to claim 1, wherein the biological sample is at least one of exfoliated cells, cervical mucus, saliva, body fluids or exhaled breath.

6. The process according to claim 1, wherein the treatment solution is a washing solution.

7. A process for recovering a treated biological sample, comprising the following steps:
   a) providing a device for collection and treatment of biological samples comprising:
      a receptacle comprising at a bottom end of the receptacle a protuberance and one or more holes;
      a cover for the receptacle, comprising a pierceable portion to permit introduction of a pipette tip, the cover comprising a collection instrument extending from a bottom of the cover and that extends into the receptacle when the receptacle is closed by the cover; and
      a tube that contacts with the bottom end of the receptacle when assembled with the receptacle;
   b) contacting at least a portion of the collection instrument with anogenital, oropharyngeal or respiratory areas of origin of a biological sample to be treated;
   c) inserting the collection instrument comprising the biological sample to be treated into the receptacle;
   d) assembling the receptacle comprising the collection instrument onto the tube and connecting the cover;
   e) piercing the pierceable portion of the cover and introducing a treatment solution into the receptacle to treat the biological sample;
   f) centrifuging the device;
   g) recovering the treated biological sample at a bottom of the tube.

* * * * *